(12) United States Patent
Lo et al.

(10) Patent No.: US 9,380,948 B1
(45) Date of Patent: Jul. 5, 2016

(54) SYSTEM AND METHOD FOR QUANTITATIVE ANALYSIS OF RESPIRATORY SINUS ARRHYTHMIA

(71) Applicants: Men-Tzung Lo, Jhongli (TW); Yung-Hung Wang, Jhongli (TW)

(72) Inventors: Men-Tzung Lo, Jhongli (TW); Chen Lin, Jhongli (TW); Cheng-Yen Wang, Jhongli (TW); Yung-Hung Wang, Jhongli (TW); Yi-Chung Chang, Jhongli (TW); Han-Hwa Hu, Taipei (TW); Kun Hu, Jhongli (TW)

(73) Assignees: Men-Tzung Lo, Jhongli (TW); Yung-Hung Wang, Jhongli (TW)

( * ) Notice: Subject to any disclaimer, the term of this patent is extended or adjusted under 35 U.S.C. 154(b) by 474 days.

(21) Appl. No.: 13/950,702

(22) Filed: Jul. 25, 2013

(51) Int. Cl.
*A61B 5/00* (2006.01)
*A61B 5/0205* (2006.01)

(52) U.S. Cl.
CPC ............ *A61B 5/0205* (2013.01); *A61B 5/7253* (2013.01)

(58) Field of Classification Search
CPC ............................ A61B 5/0205; A61B 5/7253
See application file for complete search history.

(56) References Cited

U.S. PATENT DOCUMENTS

| | | | | |
|---|---|---|---|---|
| 4,720,678 | A * | 1/1988 | Glover | G01R 33/56509 324/309 |
| 6,305,943 | B1 * | 10/2001 | Pougatchev | A61B 5/486 434/238 |
| 2004/0127804 | A1 * | 7/2004 | Hatlesad | A61B 5/0205 600/513 |

OTHER PUBLICATIONS

Kuo et al, Quantification of Respiratory Sinus Arrhythmia Using Hilbert-Huang Transform, Advances in Adaptive Data Analysis, vol. 1, No. 2 (2009), 295-307.*

* cited by examiner

*Primary Examiner* — Jacqueline Cheng
*Assistant Examiner* — Angeline Premraj
(74) *Attorney, Agent, or Firm* — SV Patent Service

(57) ABSTRACT

A computer-assisted method for quantitative analysis of respiratory sinus arrhythmia (RSA) includes obtaining a time series of a cardiac interval signal from an individual, obtaining a time series of a respiratory signal from the individual; decomposing the cardiac interval signal into a first group of ensemble empirical modes; obtaining, by a computer system, a time series of RSA instantaneous amplitude from at least one of the first group of ensemble empirical modes; decomposing the respiratory signal into a second group of ensemble empirical modes; obtaining a time series of respiratory instantaneous phase from the one of the second group of ensemble empirical modes; determining respiratory period from the time series of the respiratory instantaneous phase; and quantifying RSA in the individual according to a dependence of the RSA instantaneous amplitude on the respiratory period.

19 Claims, 9 Drawing Sheets

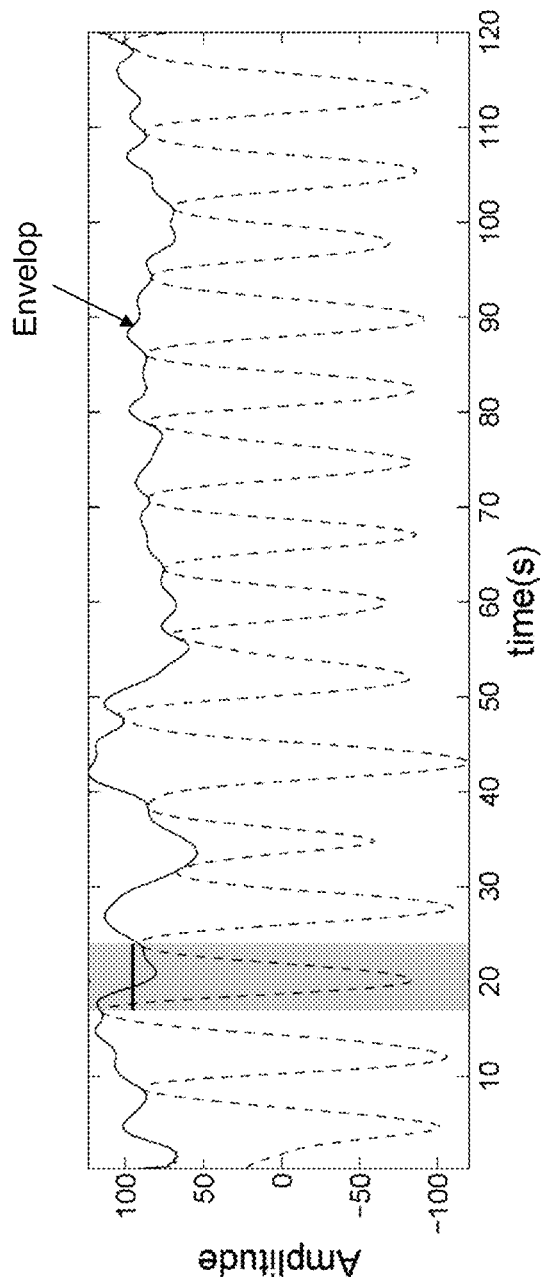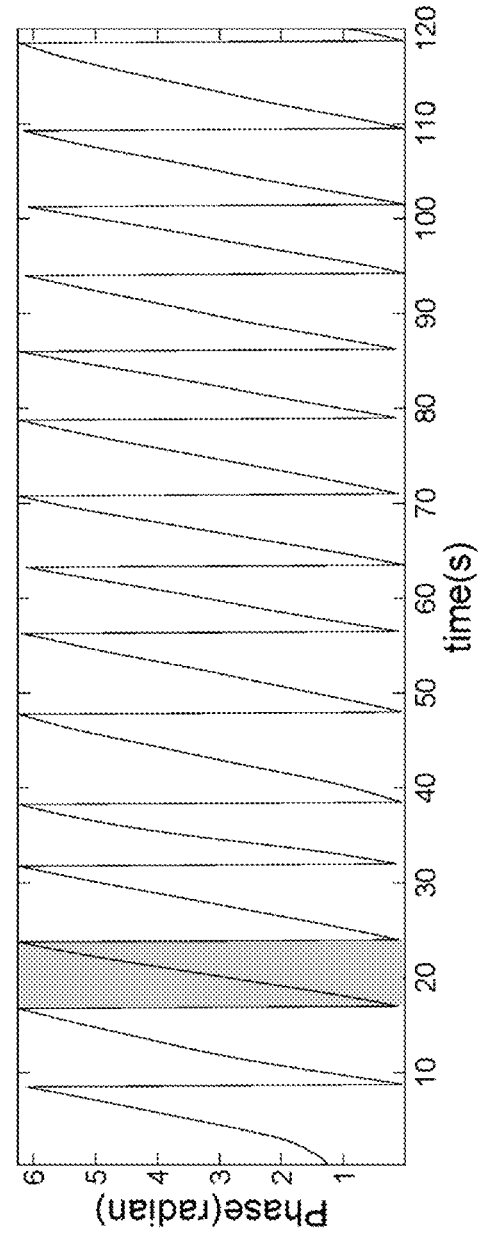
Fig. 4A
Fig. 4B

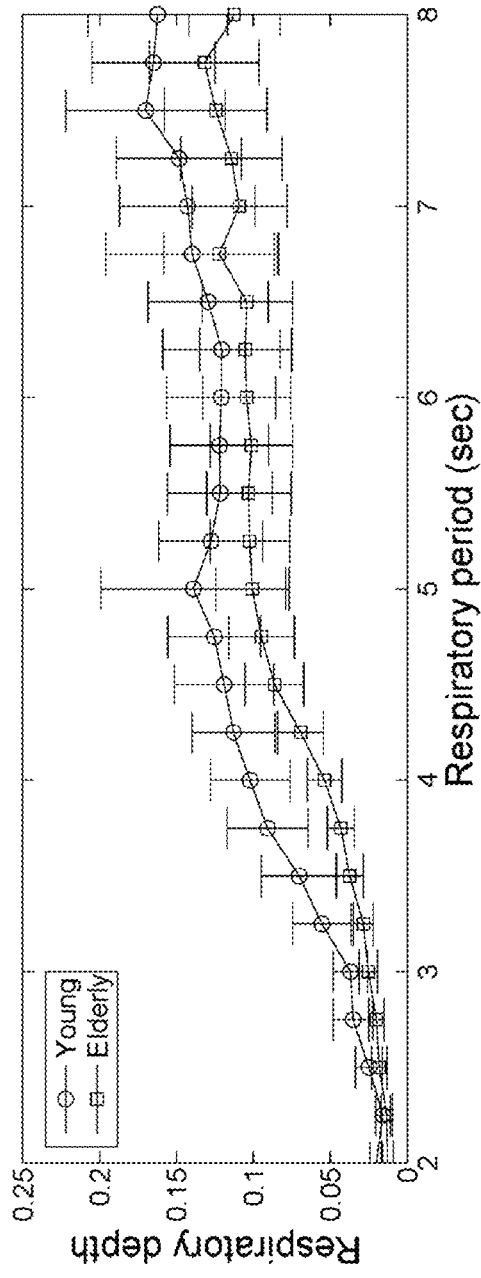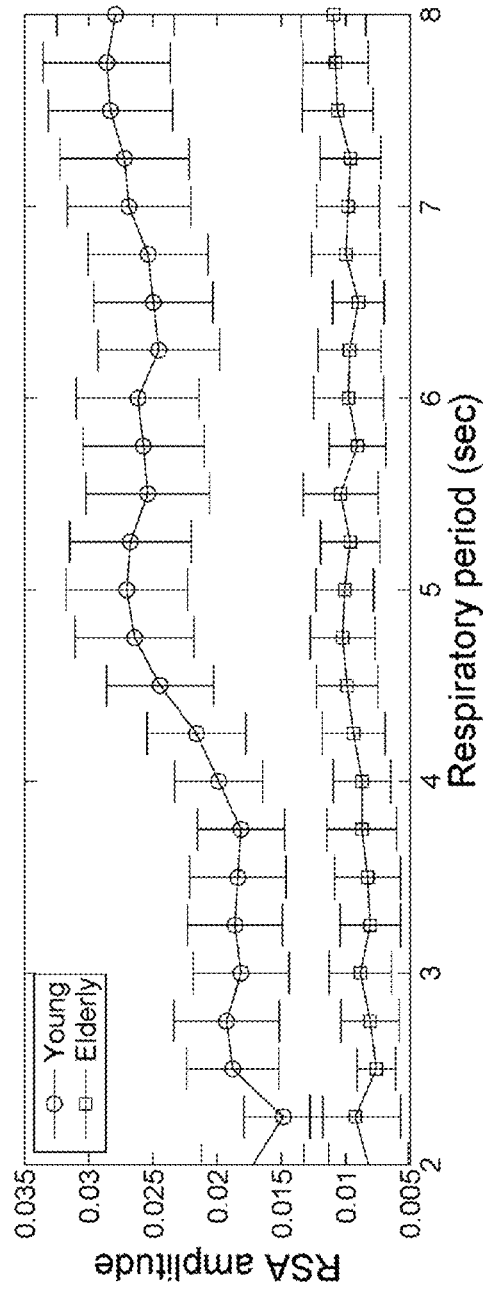
Fig. 5A
Fig. 5B

SYSTEM AND METHOD FOR QUANTITATIVE ANALYSIS OF RESPIRATORY SINUS ARRHYTHMIA

BACKGROUND OF THE INVENTION

The present application relates to analyses of physiological signals for disease diagnosis and health enhancement, and in particular, to quantitative analysis of respiratory sinus arrhythmia.

The autonomic nervous system, comprised of sympathetic and parasympathetic components, plays a major role in maintaining a system's homeostasis with flexibility and stability. Deterioration of the autonomic-related regulatory mechanisms, especially the parasympathetic-mediated ones, has been recognized in various diseases, including fatal diseases such as acute myocardiac infarction, and chronic systemic diseases such as congestive heart failure, hypertension, and diabetes, as well as in physiologic aging process. To quantitatively evaluate the autonomic function, external perturbations are frequently applied to elicit the corresponding responses of specific physiological mechanisms. For example, cardiovascular parameters (e.g., heart rate and blood pressure) alter in response to valsalva maneuver. Alternatively, autonomic function can also be assessed without external perturbation. One example is by evaluating respiratory sinus arrhythmia (RSA), that is, the instantaneous variations in heart rate induced by breathing (which are mainly attributed to respiratory elicited wax and wane of changes in vagal activities). The greater the cyclic variations of the heart rate fluctuation, the stronger the vagus nerve activities. The noninvasive nature of assessing RSA provides an attractive option to quantify the parasympathetic function without potential complication.

RSA is a naturally occurring variation in heart rate that occurs during a breathing cycle. RSA is also a measure of parasympathetic nervous system activity—which denotes "rest and digest" behaviors. Vagal tone cannot be directly measured. Instead, other biological processes are measured that represent the functionality of vagal tone. An increase in vagal tone both slows the heart and makes heart rate more variable (i.e. there is more beat-to-beat change between heart beats). During the process of RSA inhalation temporarily suppresses vagal activity, causing an immediate increase in heart rate. Exhalation then decreases heart rate and causes vagal activity to resume. RSA is pronounced in children, but it typically decreases as a person approaches their teenage years. However, adults in excellent cardiovascular health, such as endurance runners, swimmers, and cyclists, are likely to have a more pronounced RSA.

Respiratory-related oscillations of heart rate dynamics can be quantified by various methods, among which, power spectrum analysis is the most widely used approach. Power spectrum analysis is based on the simple mathematical assumption that a temporal fluctuation can be modeled by a set of superimposed sinusoidal oscillations. The temporal change of heart rate in response to spontaneous physiological, mechanical, or pharmacological perturbations can be estimated in the frequency domain. Therefore, the amount of spectral power within a specific frequency band is considered to represent the corresponding changes of the underlying mechanisms or their responses to the interventions. The spectral power of heart rate time series in a high frequency (HF) band is used to quantify the RSA. The high frequency band corresponds to the total variance of inter-beat R-R interval oscillations within normal breathing frequency ranging from 0.15 Hz to 0.40 Hz (2.5-6.7 seconds per cycle). The power spectrum analysis has been extensively employed in pharmacological, public health, and clinical fields as functional index of vagal activities.

However, power spectral analysis is unreliable in assessing RSA properties because the assumption of the method is not valid in real-world signals. First, the frequency range of the HF band constrains breathing rate within 9-24 breaths/min. In reality, the periods between breaths vary over time. The breathing activities are not sinusoidal oscillations, which introduces spurious energy spreading around the dominant frequencies and projects spectral power to outside the HF band. Secondly, RSA is not merely a phenomenon in which heart rate increases and decreases in response to respiration; RSA is also influenced by complex interactions among central, neural, hormonal, and mechanical feedback mechanisms. The complex interactions can cause intermittent interdependence between cardiac and respiratory systems, which also cause the spurious energy spreading outside the HF band. Thirdly, abrupt changes in heart rate fluctuations unrelated to RSA such as arrhythmia or irrelevant interferences such as noise can introduce power to all frequency bands of the power spectrum, thus contaminating the power in the HF band. Thus power spectral analysis based on a HF band is unreliable in estimating RSA.

There is therefore an urgent need for more accurate quantification of RSA fluctuations.

SUMMARY OF THE INVENTION

To address the aforementioned limitations, the presently invention discloses a system and method to accurately quantify RSA fluctuations. The disclosed method overcomes two important challenges in quantifying RSA fluctuations: (1) nonstationary and nonlinear nature of biological systems due to adaptations to ever-present internal and external perturbations; (2) unrelated interferences that compromise assessment of the magnitude of RSA. The presently disclosed method can more accurately characterize dynamics of the cardio-respiratory interactions mediated by vagal nerve than conventional methods. The presently disclosed method is non-invasive, and can be calculated real time. The presently disclosed method can significantly improve RSA diagnoses and provide respiratory enhancement in individuals.

In one general aspect, the present invention relates to a computer-assisted method for quantitative analysis of respiratory sinus arrhythmia (RSA). The computer-assisted method includes: obtaining a time series of a cardiac interval signal from an individual; obtaining a time series of a respiratory signal from the individual; decomposing the cardiac interval signal into a first group of ensemble empirical modes; obtaining, by a computer system, a time series of RSA instantaneous amplitude from at least one of the first group of ensemble empirical modes; decomposing the respiratory signal into a second group of ensemble empirical modes; obtaining a time series of respiratory instantaneous phase from the one of the second group of ensemble empirical modes; determining respiratory period from the time series of the respiratory instantaneous phase; and quantifying RSA in the individual at least in part according to a dependence of the RSA instantaneous amplitude on the respiratory period.

Implementations of the system may include one or more of the following. The computer-assisted method can further include calculating a standard deviation or an envelope of the RSA instantaneous amplitude to quantify the degree of RSA in the individual. The computer-assisted method can further include obtaining, by the computer system, a time series of RSA instantaneous phase from at least one of the first group of ensemble empirical modes; and quantifying RSA in the individual at least in part according to a dependence of the RSA instantaneous phase on the respiratory instantaneous phase. The computer-assisted method can further include obtaining, by the computer system, a time series of respiratory instantaneous amplitude from at least one of the second group of ensemble empirical modes; and quantifying RSA in the individual at least in part according to a dependence of the respiratory instantaneous amplitude on the respiratory period. The step of obtaining, by a computer system, a time series of RSA instantaneous amplitude can include: selecting at least one in the first group of ensemble empirical modes that is associated with a dominant respiratory frequency in the respiratory signal. The dominant respiratory frequency can reside in a frequency band from approximately 0.1 Hz to approximately 0.6 Hz. The computer-assisted method can further include removing noise from the selected at least one in the first group of ensemble empirical modes. The step of obtaining, by a computer system, a time series of RSA instantaneous amplitude further comprises: applying a Hilbert transform to the selected one in the first group of ensemble empirical modes to produce the RSA instantaneous amplitude.

In another general aspect, the present invention relates to a computer-assisted method for quantitative analysis of respiratory sinus arrhythmia (RSA). The computer-assisted method includes: obtaining a time series of a cardiac interval signal from an individual; decomposing the cardiac interval signal into a first group of ensemble empirical modes; obtaining, by a computer system, a time series of RSA instantaneous amplitude from at least one in the first group of ensemble empirical modes; obtaining a time series of RSA instantaneous phase from at least one in the first group of ensemble empirical modes; determining a respiratory period from the time series of the RSA instantaneous phase; and quantifying RSA in the individual, at least in part, according to a dependence of the RSA instantaneous amplitude on the respiratory period.

Implementations of the system may include one or more of the following. The computer-assisted method can further include calculating a standard deviation or an envelope of the RSA instantaneous amplitude to quantify the degree of RSA in the individual. The computer-assisted method can further include: obtaining a time series of a respiratory signal from the individual; and decomposing the respiratory signal into a second group of ensemble empirical modes. The computer-assisted method can further include: obtaining a time series of respiratory instantaneous phase from the one of the second group of ensemble empirical modes; and quantifying RSA in the individual at least in part according to a dependence of the RSA instantaneous phase on the respiratory instantaneous phase. The computer-assisted method can further include obtaining, by the computer system, a time series of respiratory instantaneous amplitude from at least one of the second group of ensemble empirical modes; and quantifying RSA in the individual at least in part according to a dependence of the respiratory instantaneous amplitude on the respiratory period. The step of obtaining, by a computer system, a time series of RSA instantaneous amplitude can include: selecting at least one in the first group of ensemble empirical modes that is associated with a dominant respiratory frequency. The dominant respiratory frequency can reside in a frequency band from approximately 0.1 Hz to approximately 0.6 Hz. The step of obtaining, by a computer system, a time series of RSA instantaneous amplitude can further include applying a Hilbert transform to the selected one in the first group of ensemble empirical modes to produce the RSA instantaneous amplitude.

In another general aspect, the present invention relates to a computer-assisted method for enhancing an individual's breathing pattern based on quantitative analysis of respiratory sinus arrhythmia (RSA). The computer-assisted method includes obtaining a time series of a cardiac interval signal from an individual; obtaining a time series of a respiratory signal from the individual, wherein the respiratory signal can include multiple respiratory periods; decomposing the cardiac interval signal into a first group of ensemble empirical modes by a computer system; obtaining a time series of RSA instantaneous amplitude from at least one in the first group of ensemble empirical modes; and producing an RSA signal in real time to the individual, to allow the individual to adjust and improve his or her breathing pattern, wherein RSA signal is based on at least in part the RSA instantaneous amplitude over successive respiratory periods.

Implementations of the system may include one or more of the following. The RSA signal comprises a visual signal, an audio signal, a mechanical signal, or a thermal signal. The computer-assisted method can further include decomposing the respiratory signal into a second group of ensemble empirical modes; and obtaining a time series of respiratory instantaneous phase from the one of the second group of ensemble empirical modes, wherein the respiratory periods can be obtained from the time series of the respiratory instantaneous phase. The computer-assisted method can further include obtaining a time series of RSA instantaneous phase from at least one in the first group of ensemble empirical modes, wherein the respiratory periods can be obtained from the time series of the RSA instantaneous phase. The step of obtaining a time series of RSA instantaneous amplitude can include selecting at least one in the first group of ensemble empirical modes that is associated with a dominant respiratory frequency in the respiratory signal.

These and other aspects, their implementations and other features are described in detail in the drawings, the description and the claims.

BRIEF DESCRIPTION OF THE DRAWINGS

FIG. 4A shows the envelope (solid line on top) associated with the instantaneous amplitude (dashed line) of the IMF associated with the respiratory modulation extracted from the cardiac interval signal in FIG. 3A.

FIG. 4B shows instantaneous phase of the selected IMF associated with respiratory modulation extracted from the cardiac interval time series in FIG. 3A.

FIGS. 5A-5C show cardio-respiratory relationship in a group of elderly individuals and a group of young individuals.

DETAILED DESCRIPTION OF THE INVENTION

Figure 1:
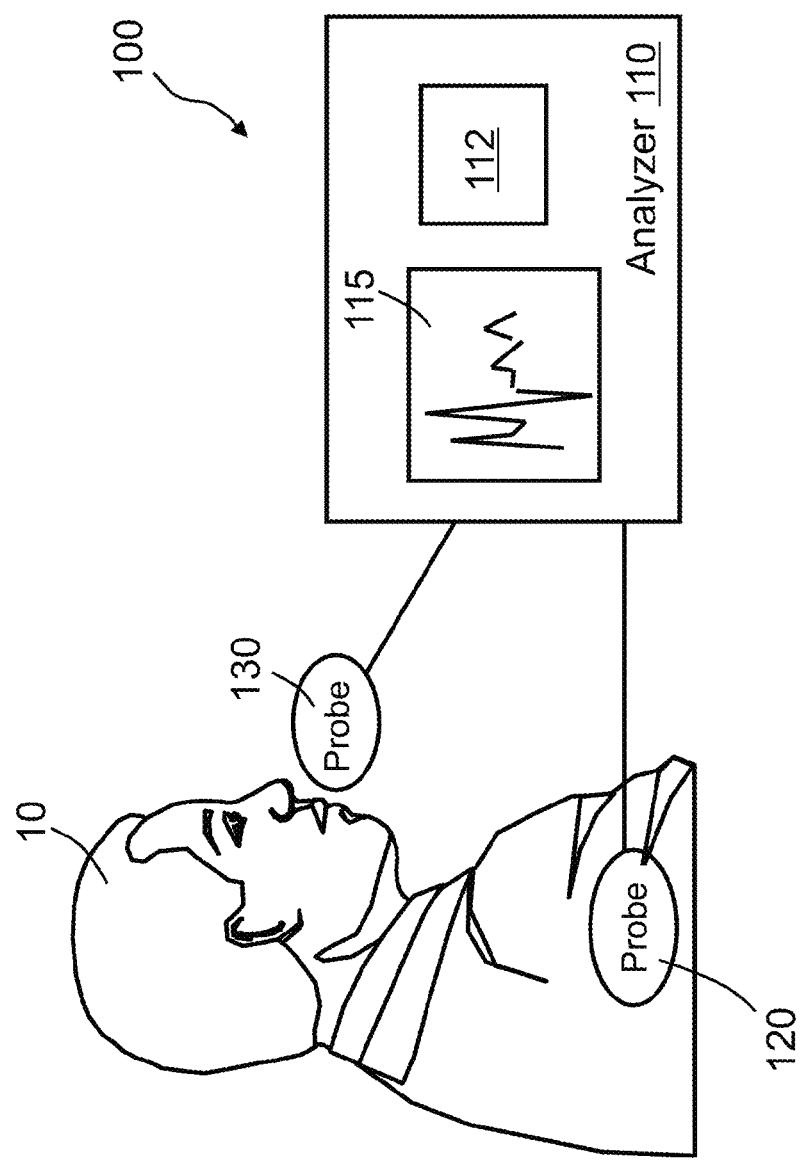
FIG. 1 is a schematic diagram illustrating an exemplified system for quantitatively evaluating RSA in accordance with the present invention.

Referring to FIG. 1, a respiratory sinus arrhythmiadetection (RSA) quantitative analysis system 100 includes an analyzer 110 and probes 120, 130 that can be attached to an individual 10. The probes 120, 130 include transducers and sensors that are configured to measure respiratory and cardio signals from the individual 10. Examples suitable for the probes 120, 130 include electrocardiography, breath sensor . . . , and so on. In some cases, a respiratory signal can be reconstructed from the electrocardiogram. The analyzer 110 can include an analog-to-digital (A/D) converter for digitizing the sensing signals which are typically in analog form. The analyzer 110 also includes a computer processor 112 that is configured to process and analyze the sensing signals after they are digitized by the A/D converter. An algorithm can be pre-stored in a computer memory in the analyzer 110 for analyzing the sensing signals. The analyzer 110 can also include input/output devices that allow a user to enter instructions to process the data, and a display 115 for displaying the raw sensing signals and data calculated from the sensing signals. The RSA quantitative analysis system 100 can be implemented as a portable unit for conducting analysis and diagnosis on site.

It is known that the heart rate can be modulated by respiratory process; the magnitude of RSA can correlate with cardiac vagal tone. Consequently, an accurate assessment of RSA requires a quantitative measure of the effects of respiratory activities on the heart rate. Such quantitative measure is a challenging task because respiratory and cardio signals are non-stationary and non-linear. Physiological recordings are also often contaminated by environmental noises, or artifacts in data acquisition (e.g. missing data or outliers), or nonstationarity introduced by the measurement itself. They can be disturbed by other coexisting physiological influences. Such artifacts are distributed over a wide range in the frequency domain, which cannot be effectively extracted by Fourier transform.

In the present disclosure, ensemble/empirical mode decomposition (EMD or EEMD) is applied to respiratory and cardio signals to produce a plurality of intrinsic mode functions (IMFs) each associated with a frequency band. The IMFs that are relevant to respiratory-cardio coupling are selected for further quantitative analysis. In EMD/EEMD, an artifact affects the IMFs locally in the time domain, and can be filtered out before further quantitative analysis. Thus the presently disclosed method is less affected by irrelevant interferences.

Figure 2:
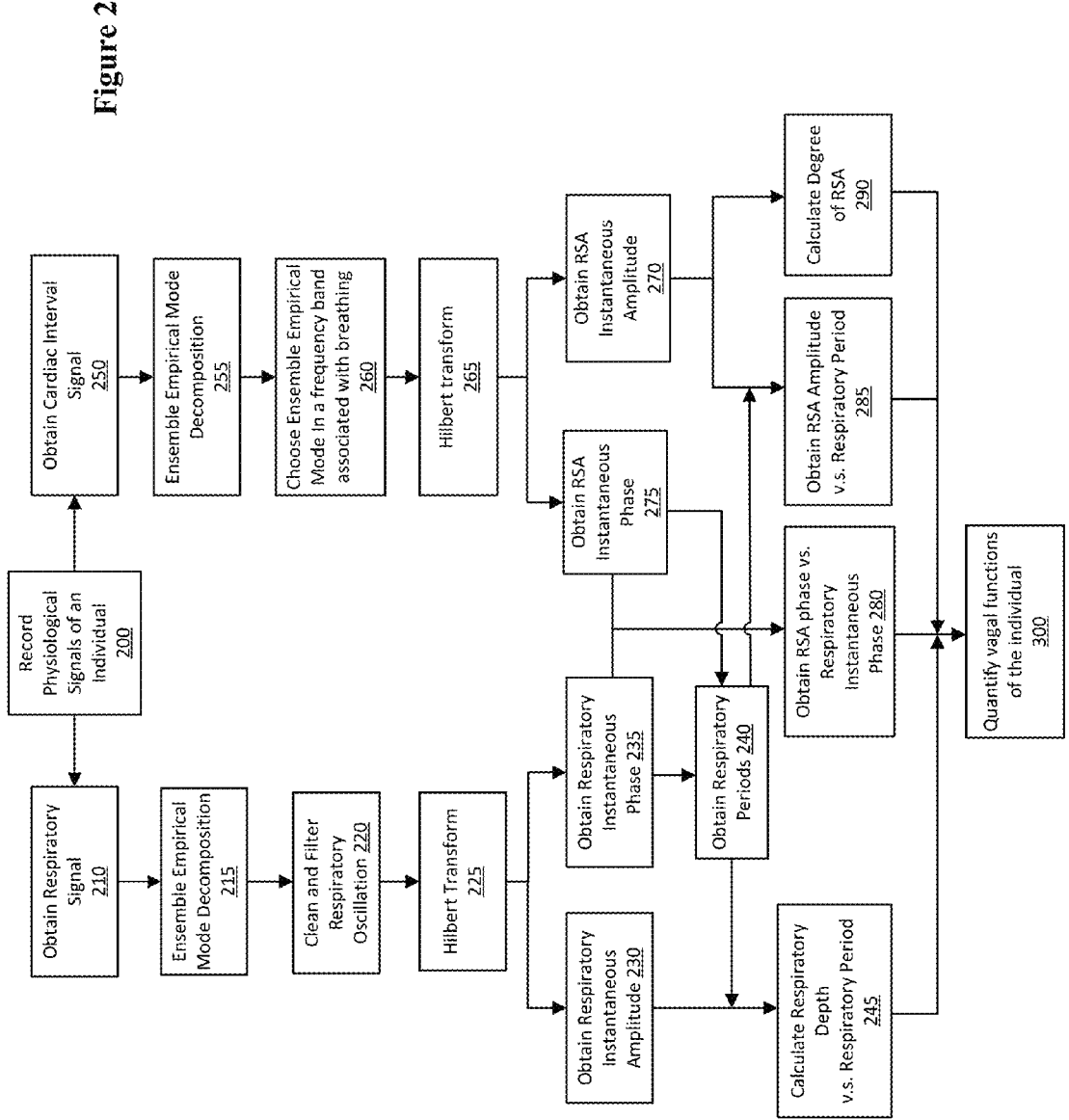
FIG. 2 is a flow diagram for quantitatively evaluating RSA in accordance with the present invention.

FIG. 2 is a flow diagram for quantitatively evaluating RSA in accordance with the present invention. Physiological signals are recorded (step 200) on an individual using the RSA quantitative analysis system (e.g. 100 described above in FIG. 1). The physiological signals recorded can include a respiratory signal (step 210) and a cardiac interval signal (step 250). To quantize vagal function, the cardio-respiratory coupling is examined under different respiratory conditions. The respiratory signal is decomposed into IMFs corresponding to ensemble empirical modes (step 215). The respiratory oscillation is cleaned by removing background noise and irrelevant artifacts (step 220). The IMFs of the respiratory signal are filtered to select dominant mode (step 220). After cleaning, Hilbert transform is conducted on the selected IMFs of the ensemble empirical modes, which has the dominant respiratory power in the respiratory signal (step 225).

The Hilbert transform provides instantaneous amplitude and instantaneous phase of an oscillation. For a time series s(t), its Hilbert transform is defined as $$\tilde{s}(t) = \frac{1}{\pi} P \int \frac{s(\tau)}{t-\tau} d\tau \qquad (1)$$

where P denotes the Cauchy principal value. For any signal s(t), the corresponding analytic signal can be constructed by its Hilbert transform and the original signals:

$$z(t) = s(t) + i \cdot \tilde{s}(t) = A(t)e^{i\varphi(t)} \qquad (2)$$

where A(t) and φ(t) are the instantaneous amplitude and phase of s(t), respectively.

The instantaneous amplitude and instantaneous phase of the respiratory signal are respectively obtained (steps 230, 235). The amplitude of respiratory signal can also be referred to as "respiratory depth". The time series of the respiratory signal is separated into cycles using the respiratory instantaneous phase. The respiratory period is obtained from the lengths of the respiratory cycles (step 240). The dependence of the respiratory depth on the respiratory period is calculated (step 245) (examples shown in FIG. 5A) in part to quantify vagal functions or RSA of an individual (step 300).

Figure 3A:
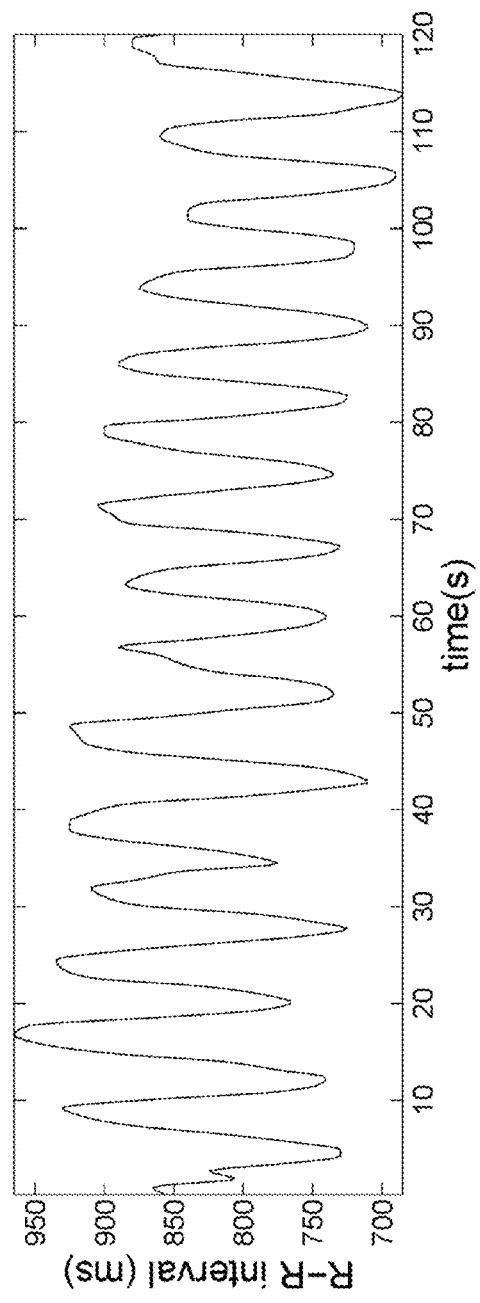
FIG. 3A shows a time series of inter-beat (R-R) interval in a heart beat signal in an individual.
Figure 3B:
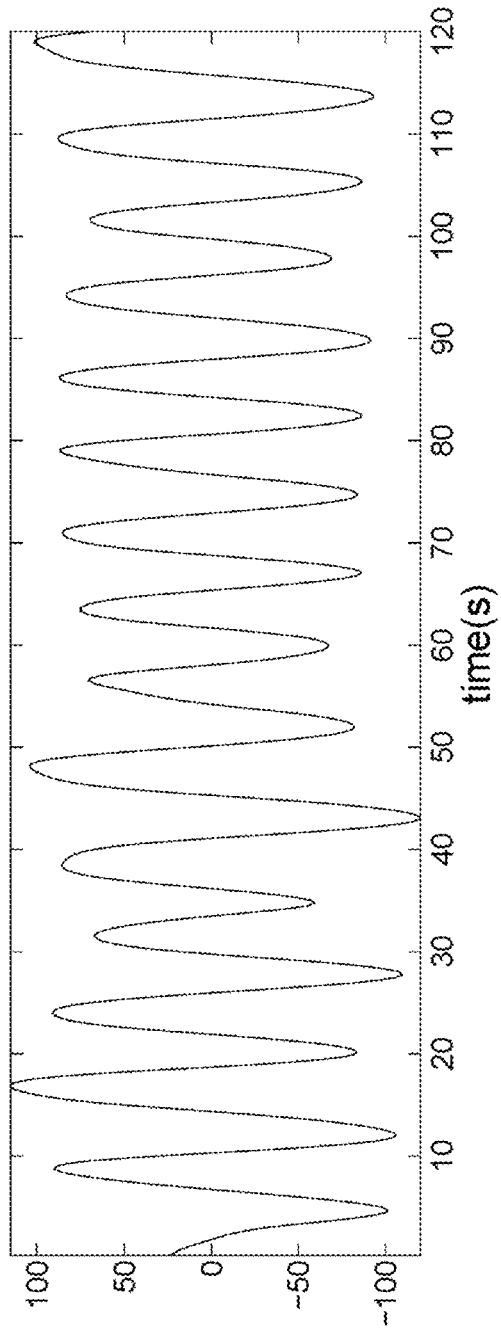
FIG. 3B shows a time series of respiratory mediated components extracted from the heat beat signal in FIG. 3A in the individual.
Figure 3C:
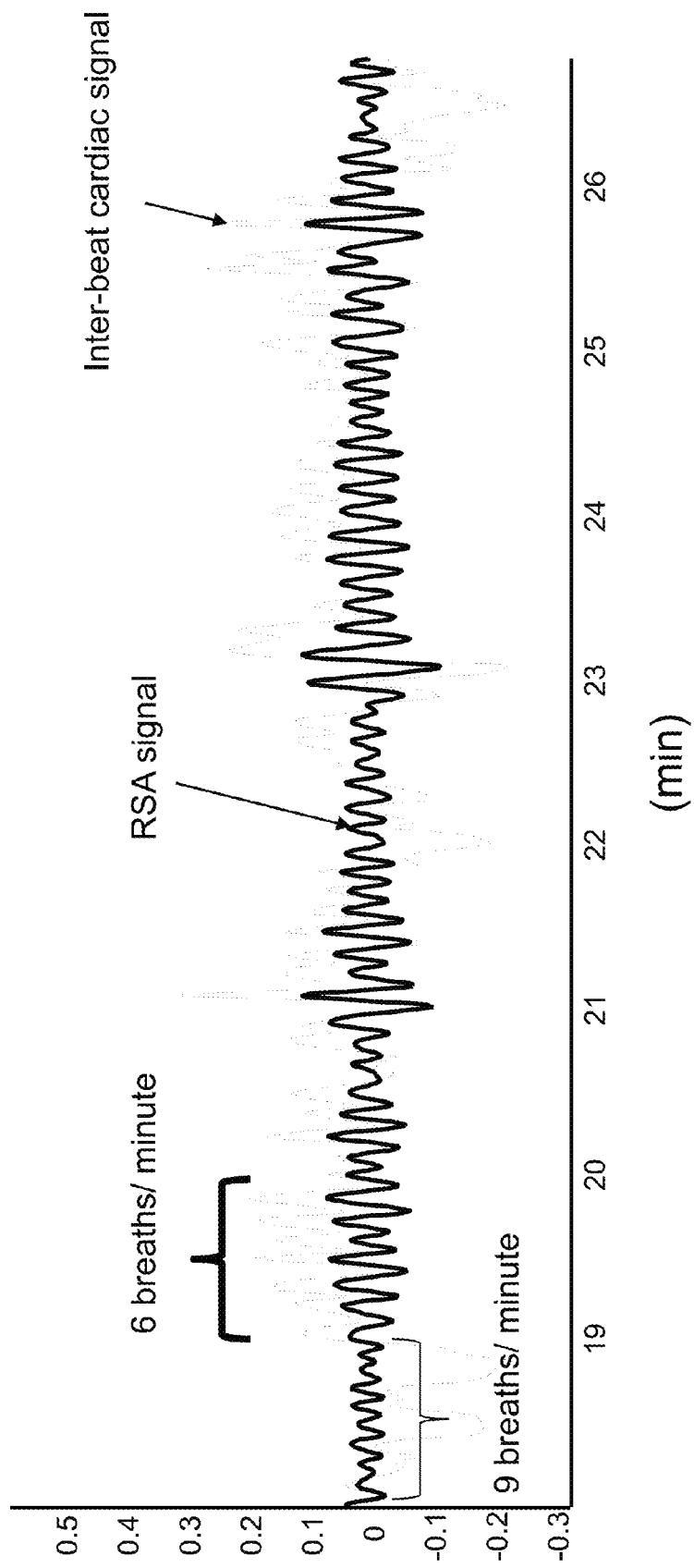
FIG. 3C shows impact of breath rate on vagal activity by an overlay of an inter-beat (R-R) interval signal (similar to FIG. 3A) and an RSA signal (similar to FIG. 3B) over a longer time period.

FIG. 3A shows the R-R interval series from a cardiac signal of an individual (step 250, FIG. 2). Each of the IMF is characterized by a frequency band (or range). The cardiac interval signal is decomposed into ensemble empirical modes each associated with an IMF (255, FIG. 2). The IMF(s) of the cardiac interval signal in the frequency band approximately 0.1 Hz to approximately 0.6 Hz (or approximately 0.15 Hz to approximately 0.4 Hz) corresponding to the respiratory signal is selected (step 260, FIG. 2). FIG. 3B shows an exemplified time series of respiratory mediated components extracted from the cardiac interval signal (step 260, FIG. 2) in FIG. 3A. The EMD and the selection of IMFs in the respiratory and cardiac interval signals can be considered as pre-processing operations for quantitative representation of RSA. FIG. 3C shows impact of breath rate on vagal activity by an overlay of an inter-beat (R-R) interval signal (similar to FIG. 3A) and an RSA signal (similar to FIG. 3B) over a longer time period. FIG. 3C shows that the magnitude of RSA is impacted by breath rate: the lower the breath rate, the higher the degree of RSA.

Next, Hilbert transform is conducted on the ensemble empirical modes of the cardiac interval signal (step 265) to produce the instantaneous amplitude and instantaneous phase in the IMF associated with the respiratory modulation. The RSA instantaneous amplitude and RSA instantaneous phase of the cardiac interval signal are respectively obtained (steps 270, 275) from the instantaneous amplitude and instantaneous phase of the IMF associated with the respiratory modulation extracted from the cardiac interval signal. FIG. 4A shows the envelope (solid line on top) associated with the instantaneous amplitude (dashed line) of the IMF associated with the respiratory modulation extracted from the cardiac interval signal in FIG. 3A. The instantaneous amplitude or the envelope of the IMF associated with the respiratory modulation extracted from the cardiac interval signal reflects the magnitude or degree of RSA in an individual.

The instantaneous phase of the selected IMF associated with respiratory modulation extracted from cardiac interval time series (i.e. the RSA instantaneous phase) is shown in FIG. 4B. The RSA instantaneous phase is used to divide the IMF into individual cycles characterized by a respiratory period, i.e., each cycle corresponds to a 360° phase increment such as from 0° to 360° and from 360° to 720°. The phases in FIG. 4B range between 0 and $2\pi$ in unit of radian, which corresponds to 0° to 360°. Each cycle is reset back to the range 0° to 360°, which can be used to determine cycles and periods in the cardiac interval time (step 240, FIG. 2).

In some embodiments, respiratory cycles and periods can be obtained from the respiratory instantaneous phase (obtained in step 235, FIG. 2) using a similar procedure as described above.

The dependence of the RSA phase on the respiratory instantaneous phase (obtained from step 235) can be calculated (step 280) as another measure to quantify vagal functions or RSA in the individual (step 300).

At the dominate respiratory frequency, the mean values of the instantaneous RSA amplitude (obtained in step 270 in FIG. 2) as a function of the respiratory periods are used as indicators to evaluate dynamical cardiac respiratory coupling at different time scales. The relationship between the RSA instantaneous amplitude and the respiratory period is obtained (step 285) using the results in steps 240, 270 as another measure to quantify vagal functions or RSA in the individual (step 300) (examples shown in FIG. 5B, 6A-6D below). The degree, that is, the standard deviation, of the RSA can be calculated (step 290) as an additional measure to quantify vagal functions or RSA in the individual (step 300).

Figure 5C:
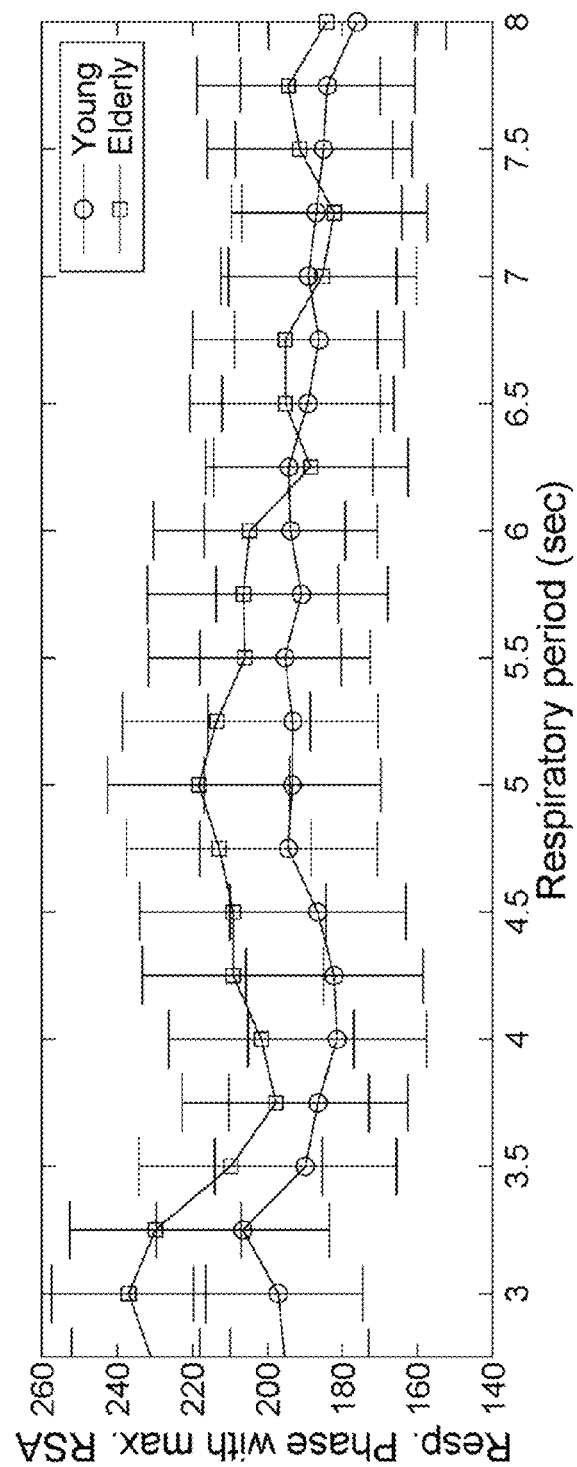
Figures 6A, 6B, 6C, 6D:
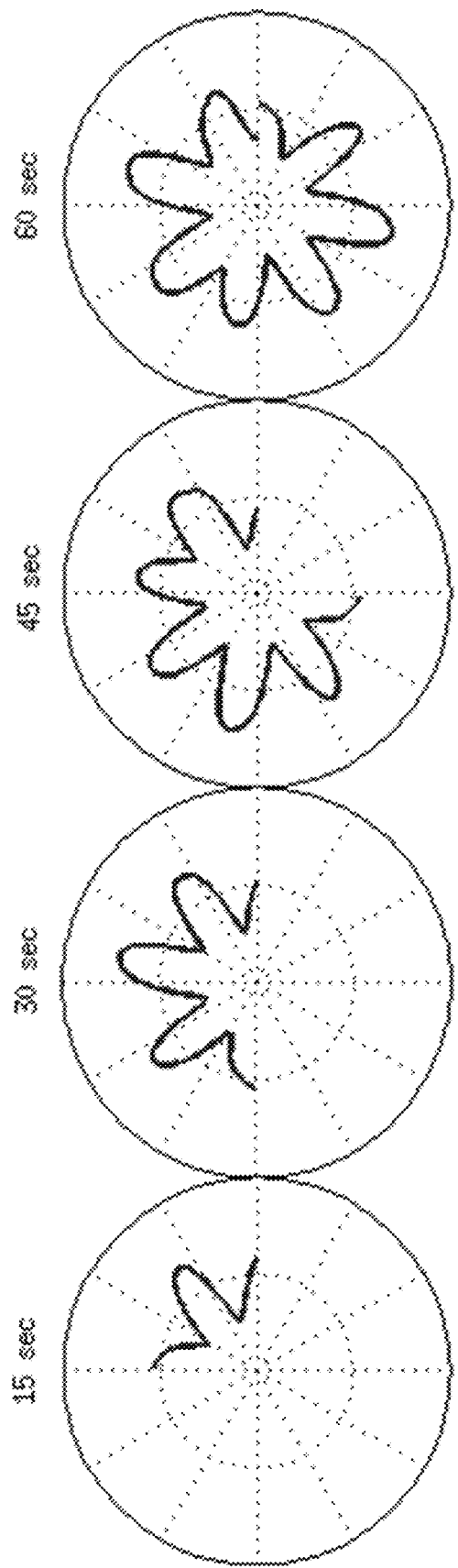
FIGS. 6A-6D display variations of RSA amplitude over successive respiratory periods in a polar coordinate.

The disclosed method has been validated. A dataset have been retrieved from in the Fantasia database, which includes two groups of individuals: twenty young (21-34 years old) and twenty elderly (68-85 years old) individuals. The dataset include inter-beat interval series and respiratory signals obtained from each individual. As described above, instantaneous phases of the respiratory signal are calculated. The time series of the respiratory signal is divided into respiratory cycles using instantaneous phase. For each respiratory period, averaged instantaneous amplitudes of the respiratory and R-R signals are calculated separately for young and elderly groups, as shown in FIGS. 5A-5C. It is found, as shown in FIG. 5B, that the amplitude of heart rate fluctuations is positively correlated with respiratory periods for young subjects. However, the cardio-respiratory relationship breaks down in the elderly subjects who display the similar heart rate fluctuation amplitude at different respiratory rate. Furthermore, as shown in FIG. 5A, the respiratory depth is not sensitive to the aging effect on cardio-respiratory coupling caused; the respiration depths have similar dependences on respiratory periods for the young and the elderly groups. Both groups show reduced respiratory depths at increased respiratory rates (i.e. decreased respiratory periods) when the rate is above ~12 cycles/minute; and relatively constant depth when the rate <12 cycles/minute). The decoupling of the gain between the respiratory-mediated heart beat fluctuation and the respiratory depth in the elderly can be a consequence of aging degeneration of autonomic function.

In some embodiments, in addition to the RSA amplitude, the phase coupling between the RSA and dominant respiratory oscillation against the different respiratory time scales (step 280, FIG. 2) is an alternative way to characterize the dynamical cardio respiratory coupling. FIG. 5C shows the respiratory phase (obtained in step 235, FIG. 2) where the magnitude of RSA reaches its maximum over different respiratory periods. For a healthy individual, the RSA phase and the instantaneous respiratory phase have an approximately 180° phase difference. However the phase lag will significantly increase (to about 240°) for elderly peoples who tend to breathe quickly (respiratory period <3.5 sec). Accordingly, variations in that phase difference between the RSA and the respiratory signals can also be used as a quantitative measure for vagal function of an individual.

In some embodiments, a standard deviation or an envelope of the instantaneous amplitude of the RSA (i.e. the degree of RSA) can be calculated to obtain a degree of RSA (step 290, FIG. 2) as a quantitative measure for vagal function of an individual.

Improvement of Vagal Function by Real-Time Feedback

A remarkable feature of the presently disclosed analysis is that it can provide RSA variations in real time, which allows immediate corrective manipulations by the individual and timely treatment by medical personnel. As described above, the current instantaneous amplitude and phase of the respiratory signals can be evaluated in each respiratory cycle. In addition, the response of RSA under different circumstances such as spontaneous or controlled breathing rate can be measured in real time, which can provide feedback to the individual's corrective effort. For example, as shown in FIGS. 6A-6D, temporal variations of RSA amplitude in successive respiratory periods can be clearly visualized in a polar coordinate. With good cardio-respiratory coupling, consistent and deep breathing produces large flower-like patterns in FIGS. 6A-6D. Apparently, the respiratory rate is easily visualized by the number and the sizes of petal: large flower petals in the polar coordinate represents consistent, healthy, and deep breathing, whereas small and incomplete petals alerts the individuals for improvement in her/his breathing patterns. This technique can be used for bio-feedback training or therapeutic treatment. With the real-time demonstration of RSA, individuals can adjust breathing patterns (pace, phase, and strength) to improve their vagal function.

Figure 7:
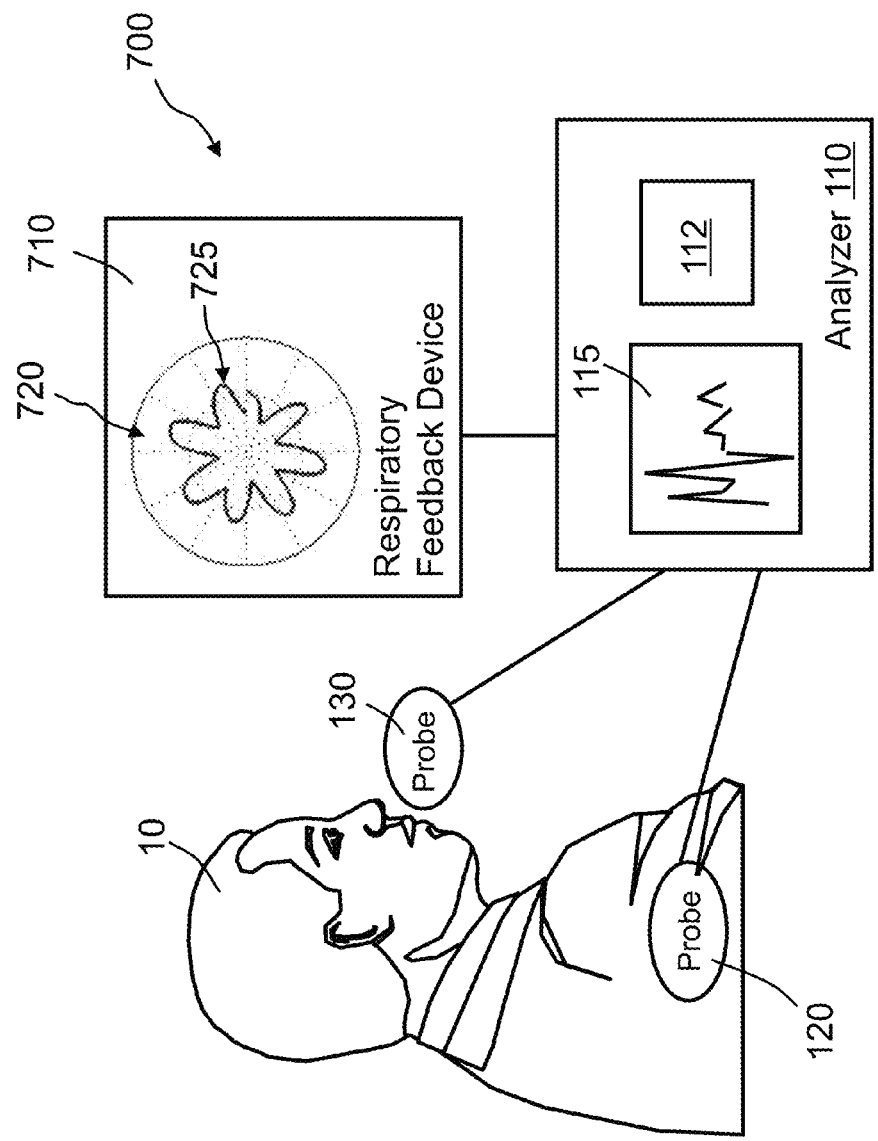
FIG. 7 illustrates an exemplified system for quantitatively evaluating RSA and enhancing an individual's respiratory function in accordance with the present invention.

The above disclosed systems and methods can be used to provide feedback to train an individual to correct, improve, and/or enhance his or her respiratory functions. Many types of feedback technologies can be used. For example, referring to FIG. 7, a respiratory enhancement system 700 includes an analyzer 110 comprising a computer processor 112, and probes 120, 130, which measures physiological signals of the individual 10 and computes quantitative assessment of the individual's RSA, as described above. An optional display 115 can be used display technical indicators (e.g. as shown in FIG. 3A-5C). The computer processor 112 sends quantitative analysis signals to a respiratory feedback device 710 to display a RSA signal 720 that is intuitive and easy to comprehend by the individual 10. Since the RSA quantitative indicators (e.g. steps 245, 280-290) can be calculated in real time, the RSA signal 720 provides a real time feedback to the individual 10 about the degree of his or her RSA over time. For example, the RSA signal 710 has several petals 725 wherein the size of petals 725 positively corresponds to the amplitude or the degree of the RSA in the individual 10: the larger the petals, the larger the magnitude of RSA is.

Upon visualizing the intuitive RSA signal 720, the individual 10 can adjust his or her breathing pattern to maximize the degree of RSA (e.g. with a goal to enlarge the petals 725). The feedback can be used as a self-guided or supervised therapeutic procedure for improving the individual's breathing pattern. After the training, the individual can breathe without the feedback while still retaining at least a portion of the improved breathing pattern.

It should be noted that in addition to visual signal, the respiratory feedback of the degree of RSA can be implemented using other techniques such as audio, mechanical movement such as vibrations, heat, etc. For example, instead of a visual display, the individual can wear a headphone to hear an audio signal representing the degree of individual's RSA. The audio signal can vary in volume, frequency, or content (e.g. types of music). For example, a higher volume, lower frequency, or certain types of soothing melody can represent consistent, healthy, and deep breathing, which allows the individual to adjust her breathing pattern to maximize the audio signal toward that direction. In another example, the individual can wear a wrist band installed with a heating device. The temperature or pulse width of the heating signal can correspond to the degree of individual's RSA. The audio or thermal signals are suitable for providing respiratory feedback in the light, or in the dark such as before or during sleep.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination.

Only a few examples and implementations are described. Other implementations, variations, modifications and enhancements to the described examples and implementations may be made without deviating from the spirit of the present invention. For example, other preprocessing or processing steps may be applied to the respiratory and cardiac signals for normalization, scaling, noise removal, etc.

What is claimed is:

1. A computer-assisted method for quantitative analysis of respiratory sinus arrhythmia (RSA), comprising:
    obtaining a time series of a cardiac interval signal from an individual using a first probe;
    obtaining a time series of a respiratory signal from the individual using a second probe;
    receiving the time series of the cardiac interval signal and the time series of the respiratory signal by an analyzer in connection with the first probe and the second probe;
    decomposing the cardiac interval signal into a first group of ensemble empirical modes using the analyzer;
    obtaining, by a computer system in the analyzer, a time series of RSA instantaneous amplitude from at least one in the first group of ensemble empirical modes;
    decomposing the respiratory signal into a second group of ensemble empirical modes;
    obtaining a time series of respiratory instantaneous phase from one of the second group of ensemble empirical modes;
    determining respiratory period from the time series of the respiratory instantaneous phase;
    quantifying RSA in the individual at least in part according to a dependence of the RSA instantaneous amplitude on the respiratory period, and
    displaying a graphic pattern on a respiratory feedback device in communication with the analyzer, wherein the graphic pattern shows dependence of the RSA instantaneous amplitude on the respiratory period,
    wherein the individual adjusts a breathing pattern to maximize amplitude of the graphic pattern and closeness to a goal of the graphic pattern to improve respiratory functions of the individual.

2. The computer-assisted method of claim 1, further comprising:
    calculating a standard deviation or an envelope of the RSA instantaneous amplitude to quantify a degree of RSA in the individual.

3. The computer-assisted method of claim 1, further comprising:
    obtaining, by the computer system, a time series of RSA instantaneous phase from at least one in the first group of ensemble empirical modes; and
    quantifying RSA in the individual at least in part according to a dependence of the RSA instantaneous phase on the respiratory instantaneous phase.

4. The computer-assisted method of claim 1, further comprising:
    obtaining, by the computer system, a time series of respiratory instantaneous amplitude from at least one of the second group of ensemble empirical modes; and
    quantifying RSA in the individual at least in part according to a dependence of the respiratory instantaneous amplitude on the respiratory period.

5. The computer-assisted method of claim 1, wherein the step of obtaining, by a computer system, a time series of RSA instantaneous amplitude comprises:
    selecting at least one in the first group of ensemble empirical modes that is associated with a dominant respiratory frequency in the respiratory signal.

6. The computer-assisted method of claim 5, wherein the dominant respiratory frequency resides in a frequency band from 0.1 Hz to 0.6 Hz.

7. The computer-assisted method of claim 5, further comprising:
    removing noise from the selected at least one in the first group of ensemble empirical modes.

8. The computer-assisted method of claim 5, wherein the step of obtaining, by a computer system, a time series of RSA instantaneous amplitude further comprises:
    applying a Hilbert transform to the selected one in the first group of ensemble empirical modes to produce the RSA instantaneous amplitude.

9. A computer-assisted method for quantitative analysis of respiratory sinus arrhythmia (RSA), comprising:
    obtaining a time series of a cardiac interval signal from an individual;
    decomposing the cardiac interval signal into a first group of ensemble empirical modes;
    obtaining, by a computer system, a time series of RSA instantaneous amplitude from at least one in the first group of ensemble empirical modes;
    obtaining a time series of RSA instantaneous phase from at least one in the first group of ensemble empirical modes;
    determining a respiratory period from the time series of the RSA instantaneous phase; and
    quantifying RSA in the individual, at least in part, according to a dependence of the RSA instantaneous amplitude on the respiratory period.

10. The computer-assisted method of claim 9, further comprising:
    calculating a standard deviation or an envelope of the RSA instantaneous amplitude to quantify a degree of RSA in the individual.

11. The computer-assisted method of claim 9, further comprising:
    obtaining a time series of a respiratory signal from the individual; and
    decomposing the respiratory signal into a second group of ensemble empirical modes.

12. The computer-assisted method of claim 11, further comprising:
    obtaining a time series of respiratory instantaneous phase from one of the second group of ensemble empirical modes; and
    quantifying RSA in the individual at least in part according to a dependence of the RSA instantaneous phase on the respiratory instantaneous phase.

13. The computer-assisted method of claim 11, further comprising:
    obtaining, by the computer system, a time series of respiratory instantaneous amplitude from at least one of the second group of ensemble empirical modes; and
    quantifying RSA in the individual at least in part according to a dependence of the respiratory instantaneous amplitude on the respiratory period.

14. The computer-assisted method of claim 9, wherein the step of obtaining, by a computer system, a time series of RSA instantaneous amplitude comprises:
    selecting at least one in the first group of ensemble empirical modes that is associated with a dominant respiratory frequency.

15. The computer-assisted method of claim 14, wherein the dominant respiratory frequency resides in a frequency band from 0.1 Hz to 0.6 Hz.

16. The computer-assisted method of claim 14, wherein the step of obtaining, by a computer system, a time series of RSA instantaneous amplitude further comprises:
    applying a Hilbert transform to the selected one in the first group of ensemble empirical modes to produce the RSA instantaneous amplitude.

17. The computer-assisted method of claim 1, further comprising:
    providing a therapeutic procedure to improve respiratory functions of the individual using the respiratory feedback device in communication with the analyzer in accordance with the dependence of the RSA instantaneous amplitude on the respiratory period.

18. The computer-assisted method of claim 1, wherein the graphic pattern includes multiple petals whose sizes are positively associated with an amplitude or a degree of the RSA in the individual.

19. The computer-assisted method of claim 18, wherein the breathing pattern is adjusted by the individual to maximize sizes and completeness of the multiple petals, wherein the amplitude of each petal is its size and the goal of each petal is its completeness.

* * * * *